United States Patent
Park et al.

(10) Patent No.: US 8,431,762 B2
(45) Date of Patent: *Apr. 30, 2013

(54) PRODUCTION OF HIGH PURITY BUTENE-1 FROM C4 OLEFINS/PARAFFINS MIXED GAS

(75) Inventors: Jong-Ho Park, Daejeon (KR); Jong-Nam Kim, Daejeon (KR); Seong-Jun Lee, Daejeon (KR); Min-Su Ko, Daejeon (KR); Hee Tae Beum, Daejeon (KR); Jongkee Park, Daejeon (KR); Chang Hyun Ko, Daejeon (KR); Sang Sup Han, Daejeon (KR); Soon-Haeng Cho, Daejeon (KR)

(73) Assignees: Korea Institute of Energy Research, Daejeon (KR); SK Energy Co., Ltd, Seoul (KR)

( * ) Notice: Subject to any disclaimer, the term of this patent is extended or adjusted under 35 U.S.C. 154(b) by 758 days.

This patent is subject to a terminal disclaimer.

(21) Appl. No.: 12/593,252

(22) PCT Filed: Apr. 11, 2008

(86) PCT No.: PCT/KR2008/002038
§ 371 (c)(1),
(2), (4) Date: Sep. 25, 2009

(87) PCT Pub. No.: WO2008/133414
PCT Pub. Date: Nov. 6, 2008

(65) Prior Publication Data
US 2010/0116639 A1  May 13, 2010

(30) Foreign Application Priority Data
Apr. 25, 2007 (KR) .................. 10-2007-0040366

(51) Int. Cl.
*C07C 7/12* (2006.01)

(52) U.S. Cl.
USPC ............ 585/809; 585/802; 585/820; 585/822

(58) Field of Classification Search .................. None
See application file for complete search history.

(56) References Cited

U.S. PATENT DOCUMENTS 3,723,561 A   3/1973   Priegnitz
4,119,678 A * 10/1978 Neuzil et al. .............. 585/366

(Continued)

FOREIGN PATENT DOCUMENTS

EP   0751106 A1   1/1997
EP   0708070 B1   5/1999

(Continued)

OTHER PUBLICATIONS

European Search Report for European Patent Application No. 08741283.9 which corresponds to U.S. Appl. No. 12/593,252.

(Continued)

*Primary Examiner* — Tam M Nguyen
(74) *Attorney, Agent, or Firm* — LRK Patent Law Firm

(57) ABSTRACT

The present invention relates to a hybrid process comprising an adsorption process and a distillation process for the separation of butene-1 from a C4 hydrocarbon mixture gas including butene-1, trans-2-butene, cis-2-butene, normal butane, isobutane, etc. The above hybrid process comprises introducing a gaseous C4 mixture into the adsorption tower loaded with adsorbents which adsorb olefins selectively to discharge C4 paraffins to the outlet of the tower, desorbing C4 olefins selectively adsorbed in the adsorption tower to produce high purity C4 olefins mixture gas in which isobutane and normal butane was removed, and separating the high C4 olefins mixture gas (a mixture of butene-1, trans-2-butene, cis-2-butene, and a trace amount of C4 paraffins) via distillation to obtain high purity butene-1 including a trace amount of isobutane in the top of the distillation tower and obtain a mixture gas including trans-2-butene, cis-2-butene and a trace amount of normal butane in the bottom of the tower.

28 Claims, 1 Drawing Sheet

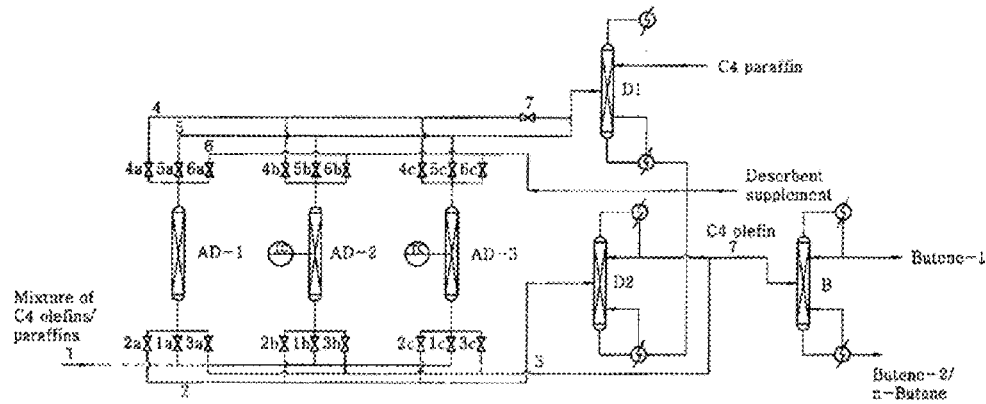

U.S. PATENT DOCUMENTS

| | | | |
|---|---|---|---|
| 4,362,537 A | | 12/1982 | Werner |
| 4,455,445 A | | 6/1984 | Neuzil et al. |
| 4,718,986 A | | 1/1988 | Comiotto et al. |
| 5,026,482 A | * | 6/1991 | Sircar ............................ 210/674 |
| 5,132,485 A | | 7/1992 | Ou |
| 5,365,011 A | | 11/1994 | Ramachandran et al. |
| 5,955,640 A | | 9/1999 | Paludetto et al. |
| 6,156,950 A | * | 12/2000 | Ragil et al. .................... 585/802 |
| 6,200,366 B1 | * | 3/2001 | Bulow et al. ..................... 95/101 |
| 6,984,765 B2 | * | 1/2006 | Reyes et al. .................... 585/639 |
| 2010/0048971 A1 | * | 2/2010 | Kim et al. ...................... 585/809 |
| 2010/0116639 A1 | * | 5/2010 | Park et al. .......................... 203/4 |

FOREIGN PATENT DOCUMENTS

| | | |
|---|---|---|
| JP | 47-38902 A | 12/1972 |
| JP | 48-62703 A | 9/1973 |
| JP | 54-41803 A | 4/1979 |
| JP | 57-197019 A | 12/1982 |
| JP | 58-065227 A | 4/1983 |
| JP | 58-126820 A | 7/1983 |
| JP | 60-51130 A | 3/1985 |
| JP | 61-115033 A | 6/1986 |
| JP | 61-126036 A | 6/1986 |
| JP | 61115033 A | 6/1986 |

OTHER PUBLICATIONS

JPO Office Action for Japanese Patent Application No. 2010-500842 which corresponds to U.S. Appl. No. 12/593,252.

International Search Report for PCT/KR2008/002038.

* cited by examiner

Fig. 1

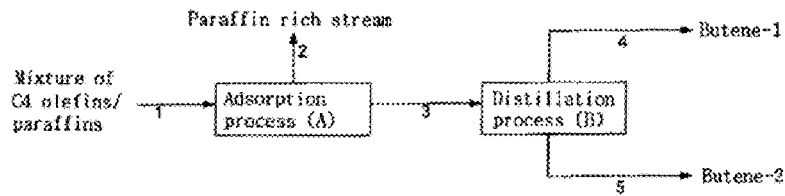

Fig. 2

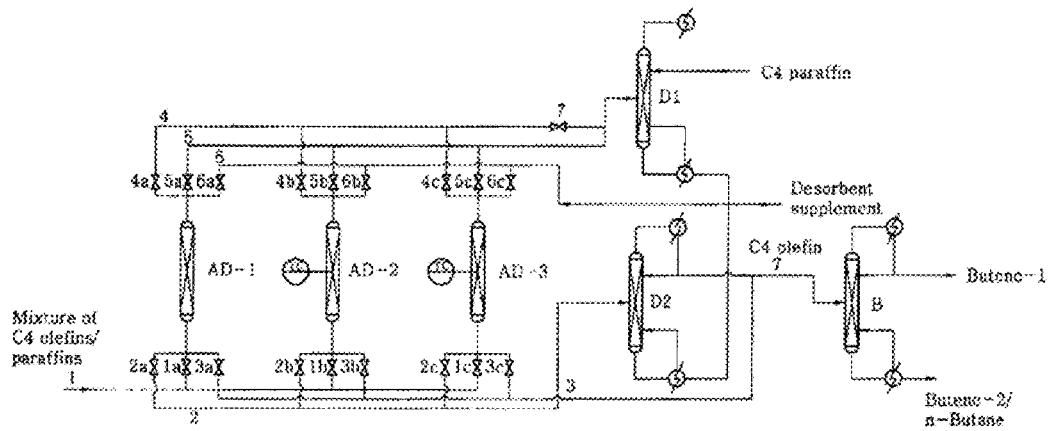

Fig. 3

| Time | t1 | t2 | t3 | t1 | t2 | t3 | t1 | t2 | t3 |
|---|---|---|---|---|---|---|---|---|---|
| AD-1 | Adsorption | Pressure equalization | Cocurrent depressurization | C4 olefin rinse | Desorption | | | Pressure equalization | Pressurization |
| AD-2 | Desorption | Pressure equalization | Pressurization | Adsorption | Pressure equalization | Cocurrent depressurization | C4 olefin rinse | Desorption | |
| AD-3 | C4 olefin rinse | Desorption | | Pressure equalization | Pressurization | Adsorption | Pressure equalization | Cocurrent depressurization | |

Fig. 4

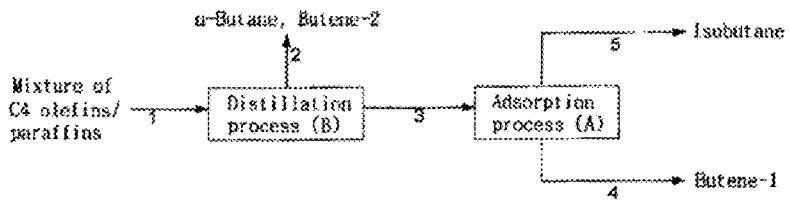

PRODUCTION OF HIGH PURITY BUTENE-1 FROM C4 OLEFINS/PARAFFINS MIXED GAS

TECHNICAL FIELD

The present invention relates to a method and its apparatus for the separation of butene-1 from a C4 hydrocarbon mixed gas including butene-1, trans-2-butene, cis-2-butene, normal butane, isobutane, etc. by using a hybrid process composed of an adsorption process and a distillation process.

BACKGROUND ART

The known method for the separation of butene-1 from a C4 hydrocarbon mixed gas including C4 olefins (butene-1, trans-2-butene, cis-2-butene, et.) and C4 paraffins (normal butane, isobutane, etc.) involves mainly a distillation process. However, the known method requires the use of distillation towers with a large number of fractionation plates due to the small boiling-point difference of the products to be separated and thus leads to high consumption of energy and to high investment costs.

TABLE 1

Boiling point of the C4 hydrocarbon mixture

| Components | Molecular weight | Boiling point (° C.) |
|---|---|---|
| Isobutane | 58.124 | −11.7 |
| Isobutene | 56.108 | −6.9 |
| Butene-1 | 56.108 | −6.3 |
| 1,3-Butadiene | 54.092 | −4.4 |
| Normal-butane | 58.124 | −0.5 |
| Trans-2-butene | 56.108 | 0.3 |
| Cis-2-butene | 56.108 | 3.7 |

U.S. Pat. No. 4,718,986 (1988) discloses a process for producing butene-1 of more than 99 wt % from the C4 hydrocarbon mixture of butene-1/isobutane/normal butane/butene-2 by using two distillation towers. According to the above patent invention, the C4 mixture is introduced into the first distillation tower to remove isobutane from the top of the tower. The lower stream from the first distillation tower is introduced into the second distillation tower, obtaining butene-1 with a purity of 99 wt % from the top of the second tower and discharging a mixture of normal butane, butene-2 and butene-1 from the bottom of the second tower. However, since a considerable amount of butene-1 is discharged with the isobutane stream from the top of the first tower and also with the mixture of normal butane, butene-2 and butene-1 from the bottom of the second tower, the above process results in much loss of butene-1.

There are a number of known techniques relating to the adsorption-separation processes for a C4 hydrocarbon mixture, for example, a technique for separating butene-1 from a mixture including butene-1/butene-2/isobutylene by using type X or Y zeolite containing potassium ion or barium ion (U.S. Pat. No. 3,723,561, Mar. 27, 1973), a technique for separating butene-1 from a liquid C4 hydrocarbon mixture by using type K-X zeolite (U.S. Pat. No. 4,119,678, Oct. 10, 1978), a technique for separating normal C4 hydrocarbon mixture and isobutylene by using a molecular sieve selective to normal C4 hydrocarbon mixture (U.S. Pat. No. 4,455,445, Jun. 19, 1984), a technique for selectively separating alfa olefin alone from olefins having more than 4 carbon atoms by a liquid adsorption process using a zeolite molecular sieve (U.S. Pat. No. 5,132,485, 1992), a pressure-swing adsorption process for the separation of olefins/paraffins having 2-6 carbon atoms in vapor phase by using type 4A zeolite (U.S. Pat. No. 5,365,011, 1994), and a technique for separating paraffins from a mixture of olefins/paraffins having 2-6 carbon atoms in vapor phase using type X or Y zeolite and reproducing the adsorbents used in the adsorption process by using desorbents (EP 0708070 B1, 1999). The U.S. Pat. No. 5,955,640 (1999) discloses a process of improving the yield of butene-1 by converting butene-2 components into butene-1 while removing a portion of paraffin components by using an adsorption process in order to prevent the accumulation of unreacted paraffin components in the process.

However, distillation using two towers connected in series as shown in the above U.S. Pat. No. 4,718,986 (1998) is the only process used for obtaining butene-1 with high purity from the C4 olefins/paraffins mixture gas. Till now, there is no adsorptive-separation techniques that can separate butene-1 with high purity from a mixture of C4 olefins/paraffins by selectively separating C4 olefin mixture gas from C4 olefins/paraffins mixture by an adsorption process and then obtaining high purity butene-1 from C4 olefin mixture gas selectively separated from the adsorption process by a distillation process, as can be achieved by the present invention.

DISCLOSURE OF INVENTION

Technical Problem

The existing distillation processes for separating betene-1 from a mixture of olefins/paraffins use two sequential distillation towers to remove isobutane from the first distillation and obtain high purity butene-1 from the second distillation tower. However, a significant amount of butene-1 is discharged together with a isobutane stream to the top of the first tower and also discharged to the bottom of the second distillation tower and thus butene-1 loss is large. In addition, since the difference in relative volatilities among C4 components is small, the above distillation processes require high consumption of energy and high investment costs.

Technical Solution

In the above circumstance, the inventors of the present invention have designed a hybrid process of removing paraffins by the C4 olefins/paraffins adsorption separation process and thereafter separating the C4 olefins via distillation to obtain high purity butene-1.

If olefins are selectively separated from the C4 olefins/paraffins mixture gas by using the adsorption separation process, the paraffin components are selectively removed, butene-1 loss which is accompanied at the time of removing isobutane can be reduced, also the concentration of the normal butane in the gas introduced into the distillation process for the production of high purity butene-1 is lowered, and thus the production of butene-1 is easy and the yield of butene-1 in the whole process increases.

Advantageous Effects

The present invention can reduce the butene-1 loss and investment costs over the process consisted only of multistage distillation tower by using a hybrid process consisted of a olefins/paraffins adsorption separation process and a olefin distillation process.

Now, some embodiments of the present invention are illustrated with reference to the drawings accompanied. However, it is understood that the illustrated embodiments of the present invention are intended to be examples only and the invention is not limited to any embodiments.

BRIEF DESCRIPTION OF THE DRAWINGS

FIG. 1 is a schematic view of the process of obtaining high purity butene-1 from a mixture gas of C4 olefins/paraffins according to the method of the present invention. The method of the present invention comprises a adsorption process (A) for separating the C4 olefins via selective adsorption and a distillation process (B) for producing butene-1 from the olefin components FIG. 2 is a schematic view of the apparatus for the production of high purity butene-1 by separating the olefins from C4 olefins/paraffins mixture gas and then distilling the C4 olefins separated according to the method of the invention.

FIG. 3 is a table showing a cycle sequence of the adsorption process (A) for selectively separating the olefins according to the method of the present invention.

FIG. 4 is a schematic view of another method of the present invention comprising the hybrid process of a adsorption process (A) and a distillation process (B).

BEST MODE FOR CARRYING OUT THE INVENTION

The present invention provides a method of performing a adsorption process for the adsorption of C4 olefins from a C4 olefins/paraffins mixture gas to obtain high purity C4 olefins mixture gas (a mixture gas including betene-1, trans-2-butene, cis-2-butene and a trace amount of C4 paraffins) and then performing a distillation process for the distillation separation of the obtained high purity C4 olefins mixture gas to obtain high purity butene-1 including a trace amount of isobutane in the top of the distillation tower and obtain a mixture gas including trans-2-butene, cis-2-butene and a trace amount of normal butane in the bottom of the tower, and an apparatus for practicing said method.

Preferably, the present invention provides a method for production of butene-1 by separating C4 olefins from a mixture gas composed of C4 olefins/paraffins via displacement desorption with desorbents (desorption agents) and then distilling the separated C4 olefins, in an apparatus including an adsorption facility composed of three adsorption towers loaded with adsorbents which adsorb olefins selectively and two distillation towers (one distillation tower for the separation of olefins/desorbents and another distillation tower for the separation of paraffins/desorbents), and a distillation tower for obtaining butene-1 by distilling C4 olefins produced from the adsorption facility, which comprises an adsorption process including an adsorption step for introducing the mixture gas of C4 olefins/paraffins into the adsorption towers loaded with olefin selective adsorbent to adsorb olefins on the adsorbents, discharge non-adsorbed paraffins and the desorbents retained in the adsorption tower to the distillation column for separation of paraffins and the desorbents through the outlet of the adsorption tower; a C4 olefin rinse step to remove a small amount of paraffins adsorbed together with olefins on the adsorbents by introducing a portion of high purity C4 olefins resulting from the distillation process of olefins/desorbents into the adsorption tower after the completion of the adsorption step and thus increasing the purity of olefins; and a desorption step of obtaining high purity olefins by introducing desorbents into the adsorption towers after the completion of the rinse step to desorb the C4 olefins and introduce the olefins/desorbents mixture to the distillation tower for the separation of the olefins and the desorbents; and a distillation process for production of butene-1 by distilling the C4 olefins obtained in the adsorption process, wherein said sequential adsorption, olefin rinse and desorption steps are repeatedly performed in each of the adsorption towers, and wherein each adsorption towers are operated to perform the different steps with each other at the same time point.

In the above method, C4 olefins/paraffins mixture gas can be firstly distilled to separate isobutane and butene-1 and discharge normal butane and butene-2 and then the resulting isobutane and butene-1 mixture can be fed into the adsorption process to obtain high purity butene-1, in place of obtaining high purity butene-1 by first processing the C4 olefins/paraffins mixture gas via the adsorption process to separate C4 olefins and then separating butene-1 from the resulting C4 olefins via the distillation process. In this case, isobutane and butene-1 are separated as paraffins and olefins respectively by the same process as said adsorption process.

The adsorption process used in the method of the present invention is a process for separating C4 olefins from a mixture gas composed of C4 olefins/paraffins by displacement desorption with desorbents (desorption agents), in a facility composed of three adsorption towers loaded with adsorbents which adsorb olefins selectively and two distillation towers (one distillation tower for the separation of olefins/desorbents and another distillation tower for the separation of paraffins/desorbents), which comprises an adsorption step for introducing the mixture gas of C4 olefins/paraffins into the adsorption towers loaded with olefin selective adsorbent to adsorb olefins on the adsorbents, discharge non-adsorbed paraffins and the desorbents retained in the adsorption tower to the distillation column for separation of paraffins and the desorbents through the outlet of the adsorption tower; a C4 olefin rinse step of cleaning a small amount of paraffins adsorbed together with olefins on the adsorbents by introducing a portion of high purity C4 olefins resulting from the distillation process of olefins/desorbents into the adsorption tower after the completion of the adsorption step and thus increasing the purity of olefins; and a desorption step of obtaining high purity olefins by introducing desorbents into the adsorption towers after the completion of the rinse step to desorb the C4 olefins and introduce the olefins/desorbents mixture to the distillation tower for the separation of the olefins and the desorbents, wherein said sequential adsorption, olefin rinse and desorption steps are repeatedly performed in each of the adsorption towers, and wherein each adsorption towers are operated to perform the different steps with each other at the same time point.

The adsorption process used in the method of the present invention may carry out a sequence of adsorption step, rinse step and desorption step in a predetermined time period in more than three adsorption towers respectively in such a way that a part of the same step overlaps to each other among the towers.

Preferably, the adsorption process used in the method of the present invention further includes a cocurrent depressurization step of discharging the paraffin component residue present in the adsorption towers before the olefin rinse step.

Also preferably, the method of the present invention further includes a pressure equalization step at which the paraffin components present in the interior of the adsorption tower after the completion of the adsorption step is transferred to the another adsorption tower which just completed the desorption step by connecting the two adsorption towers so that the pressure of the adsorption towers becomes equalized.

Also preferably, the method of the present invention further includes a cocurrent de-pressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

Also preferably, olefin selective adsorbents for use in the adsorption process of the method of the present invention is π-complex adsorbent forming π-complex selectively with olefins, type X zeolite or type Y zeolite, and preferably type 13X zeolite.

Also preferably, the adsorbent for use in the adsorption process of the method of the present invention is C5 hydrocarbon or C6 hydrocarbon.

Also preferably, in the adsorption process of the method of the present invention, the desorbent separated from the olefin/desorbent distillation tower and the paraffin/desorbent distillation tower is recirculated into adsorption tower.

Also preferably, in the adsorption process of the method of the present invention, the operating pressure of the adsorption tower in the C4 olefin/paraffin separation process is 1 to 10 atm (absolute pressure) and the temperature is 20 to 150° C.

The present invention also provides an adsorption facility and a distillation tower for separating butene-1 from C4 olefins discharged from the distillation tower (D2) in the adsorption facility.

Preferably, the present invention provides an apparatus for the separation of butene-1 from a mixture gas of C4 olefins/paraffins by carrying out repeated sequential adsorption, olefin rinse and desorption steps to separate C4 olefins from the mixture gas of C4 olefins/paraffins in such a way of performing displacement desorption with desorbents, in an adsorption facility including three adsorption towers (AD-1, AD-2 and AD-3) loaded with adsorbents which adsorb olefins selectively and two distillation towers (one distillation tower (D2) for the separation of olefins/desorbents and another distillation tower (D1) for the separation of paraffins/desorbents), and by distilling the separated C4 olefins in the distillation tower (B) to separate butene-1 from the C4 olefins, said apparatus comprising the adsorption tower (AD-1) in which the bottom of the tower is connected with the feeding conduit (1) for the mixture gas of C4 olefins/paraffins through the valve (1a), with the C4 olefin/desorbent discharging conduit (2) through the valve (2a) which is connected to the distillation tower (D2), and with the conduit (3) through the valve (3a) which feeds an amount of C4 olefins produced by the distillation tower (D2), and in which the top of the tower is connected with the conduit (4) through the valve (4a) which introduces paraffins and deserbents from the olefin rinse step into the distillation tower (D1), with the conduit (5) through the valve (5a) which feeds paraffins and desorbents discharged from the adsorption step into the distillation tower (D1), and with the conduit (6) through the valve (6a) which feeds the desorbents into the adsorption tower;

the adsorption tower (AD-2) in which the bottom of the tower is connected with the feeding conduit (1) for the mixture gas of C4 olefins/paraffins through the valve (1b), with the C4 olefin/desorbent discharging conduit (2) through the valve (2b) which is connected to the distillation tower (D2), and with the conduit (3) through the valve (3b) which feeds an amount of C4 olefins produced by the distillation tower (D2), and in which the top of the tower is connected with the conduit (4) through the valve (4b) which introduces paraffins and deserbents from the olefin rinse step into the distillation tower (D1), with the conduit (5) through the valve (5b) which feeds paraffins and desorbents discharged from the adsorption step into the distillation tower (D1), and with the conduit (6) through the valve (6b) which feeds the desorbents into the adsorption tower;

the adsorption tower (AD-3) in which the bottom of the tower is connected with the feeding conduit (1) for the mixture gas of C4 olefins/paraffins through the valve (1c), with the C4 olefin/desorbent discharging conduit (2) through the valve (2c) which is connected to the distillation tower (D2), and with the conduit (3) through the valve (3c) which feeds an amount of C4 olefins produced by the distillation tower (D2), and in which the top of the tower is connected with the conduit (4) through the valve (4c) which introduces paraffins and deserbents from the cleaning step into the distillation tower (D1), with the conduit (5) through the valve (5c) which feeds paraffins and desorbents discharged from the adsorption step into the distillation tower (D1), and with the conduit (6) through the valve (6c) which feeds the desorbents into the adsorption tower;

the distillation tower (D1) which separates C4 paraffins and desorbents introduced from the adsorption towers (AD-1, AD-2 and AD-3);

the distillation tower (D2) which separates C4 olefins and desorbents introduced from the adsorption towers (AD-1, AD-2 and AD-3); and the distillation tower (B) which separates butene-1 by distillation of the C4 olefins from the distillation tower (D2).

Preferably, the adsorption facility of the apparatus of the present invention further includes the valve (7) in the conduit (4) connected to the distillation tower (D1).

In addition, the apparatus of the present invention may include more than three adsorption towers which are adapted to carry out a sequence of adsorption step, cleaning step and desorption step in a predetermined time period in three adsorption towers respectively in such a way that a part of the same step overlaps to each other among the towers.

MODE FOR THE INVENTION

The detailed description of the invention with reference to the drawings is as follows.

FIG. 1 is a schematic view of the process constitution for separating C4 olefins from a mixture gas of C4 olefins/paraffins according to the present invention. The process of the present invention comprises an adsorption process for separating the mixture of C4 olefins/paraffins and a distillation process for separating high purity butene-1 from the C4 olefins mixture gas separated from the adsorption process. The mixture of C4 olefins/paraffins is introduced into the adsorption process through the conduit (1). The paraffin components which were not adsorbed on the adsorbents from the mixture of C4 olefins/paraffins is discharged through conduit (2), and the adsorbed olefin components is desorbed by the desorbents and introduced into the distillation process (B) through conduit (3). If the olefin mixture gas containing butene-1 and butene-2 together with small amount of isobutane and normal butane is introduced into the distillation process, butene-1 and isobutane having lower boiling points is discharged to the top (conduit (4)) of the distillation tower and normal butane and butene-2 components having relatively higher boiling points is discharged to the bottom (conduit (5)) of the distillation tower. The olefin rich mixture gas produced from the adsorption process has about 0 to 0.5 wt % level of isobutane and 0 to 5 wt % of normal butane as a much amount of isobutane and normal butane is removed. If necessary, isobutane and normal butane may be completely removed.

The hybrid process of the present invention can be described with reference to FIG. 2 including the adsorption facility composed of three adsorption towers and two distillation tower and the distillation tower (B) as follows.

The adsorption facility used in the apparatus of the invention is a facility for the separation of C4 olefins from a mixture gas of C4 olefins/paraffins, by carrying out repeated sequential adsorption, olefin rinse and desorption steps in such a way of performing displacement desorption with the desorbents to separate C4 olefins from the mixture gas, in three adsorption towers (AD-1, AD-2 and AD-3) loaded with olefin selective adsorbents and two distillation towers (one distillation tower (D2) for the separation of olefins/desorbents and another distillation tower (D1) for the separation of paraffins/desorbents), which comprises the adsorption tower (AD-1) in which the bottom of the tower is connected with the feeding conduit (1) for the mixture gas of C4 olefins/paraffins through the valve (1a), with the C4 olefin/desorbent discharging conduit (2) through the valve (2a) which is connected to the distillation tower (D2), and with the conduit (3) through the valve (3a) which feeds an amount of C4 olefins produced by the distillation tower (D2), and in which the top of the tower is connected with the conduit (4) through the valve (4a) which introduces paraffins and deserbents from the cleaning step into the distillation tower (D1), with the conduit (5) through the valve (5a) which feeds paraffins and desorbents discharged from the adsorption step into the distillation tower (D1), and with the conduit (6) through the valve (6a) which feeds the desorbents into the adsorption tower;

the adsorption tower (AD-2) in which the bottom of the tower is connected with the feeding conduit (1) for the mixture gas of C4 olefins/paraffins through the valve (1b), with the C4 olefin/desorbent discharging conduit (2) through the valve (2b) which is connected to the distillation tower (D2), and with the conduit (3) through the valve (3b) which feeds an amount of C4 olefins produced by the distillation tower (D2), and in which the top of the tower is connected with the conduit (4) through the valve (4b) which introduces paraffins and deserbents from the cleaning step into the distillation tower (D1), with the conduit (5) through the valve (5b) which feeds paraffins and desorbents discharged from the adsorption step into the distillation tower (D1), and with the conduit (6) through the valve (6b) which feeds the desorbents into the adsorption tower;

the adsorption tower (AD-3) in which the bottom of the tower is connected with the feeding conduit (1) for the mixture gas of C4 olefins/paraffins through the valve (1), with the C4 olefin/desorbent discharging conduit (2) through the valve (2c) which is connected to the distillation tower (D2), and with the conduit (3) through the valve (3c) which feeds an amount of C4 olefins produced by the distillation tower (D2), and in which the top of the tower is connected with the conduit (4) through the valve (4c) which introduces paraffins and deserbents from the cleaning step into the distillation tower (D1), with the conduit (5) through the valve (5c) which feeds paraffins and desorbents discharged from the adsorption step into the distillation tower (D1), and with the conduit (6) through the valve (6c) which feeds the desorbents into the adsorption tower;

the distillation tower (D1) which separates C4 paraffins and desorbents introduced from the adsorption towers (AD-1, AD-2 and AD-3); and the distillation tower (D2) which separates C4 olefins and desorbents introduced from the adsorption towers (AD-1, AD-2 and AD-3).

The distillation tower (B) in the present invention is a distillation tower for separating high purity butene-1 from C4 olefin mixture gas produced from the adsorption facility.

FIG. 2 is a schematic view of the apparatus of producing butene-1 from a mixture gas of C4 olefins/paraffins according to the present invention. The adsorption facility of the apparatus of the present invention comprises three adsorption towers for separating C4 olefins via selective adsorption and two distillation towers for separating C4 olefins/desorbents and C4 paraffins/desorbents respectively. The basic process of the adsorption tower used in the present invention includes an adsorption step of selectively adsorbing C4 olefins from feed, a C4 olefin rinse step of removing a small amount of C4 paraffins adsorbed together with C4 olefins; and a C4 olefin desorption step using the desorbents and the process further can includes pressure equalization step, cocurrent depressurization step, and pressurization step. The desorbent discharged from the adsorption step along with olefins or paraffins is separated in the distillation tower and then recycled into the adsorption tower. The preferable desorbents is C5 hydrocarbon or C6 hydrocarbon which has a large difference in boiling point from that of the C4 mixture.

A cycle operation of the adsorption process can be described with reference to FIG. 2 on the basis of FIG. 3 which includes the operation steps of all the preferable adsorption process as follows.

The mixture gas containing C4 olefins/paraffins is introduced into the adsorption tower (AD-1) loaded with olefin selective adsorbents through the conduit (1) and valve (1a) to adsorb C4 olefins thereon (adsorption step), and the olefin free paraffin stream separated from the mixture is introduced together with the desorbents retained in the adsorption tower before the adsorption step into the distillation tower (D1) through the conduit (5) and the valve (5a) to separate paraffins and desorbents. The adsorption tower (AD-2) carries out the step (desorption step) of desorbing olefin components with the desorbent while the adsorption tower (AD-1) carries out the adsorption step. The desorbents used in the desorption step is obtained from the bottoms of the distillation tower (D1) and the distillation tower (D2) and is introduced into adsorption tower (AD-2) through the conduit (6) and the valve (6b). The olefins discharged with the desorbents is introduced into the distillation tower (D2) through the valve (2a) and the conduit (2) to separate the olefins and the desorbents. The adsorption tower (AD-3) is provided with a portion of the olefins separated from the distillation tower (D2) through the conduit (3) and the valve (3c) to remove a small amount of paraffins adsorbed together with the olefins for the improvement of the purity of olefins (C4 olefin rinse step). At that time, the gas discharged from the adsorption tower (AD-3) is introduced into the distillation tower (D1) through the valve (4c) and the conduit (4).

The adsorption tower (AD-1) at high pressure which just carried out the adsorption step is connected with the adsorption tower (AD-2) at low pressure through the valve (4a) and the conduit (4) and thus a process (pressure equalization step) that allows the pressures of both towers to be in the same pressure is carried out. During the pressure equalization step, the valve (7) is closed. The adsorption tower (AD-3) after the rinse step carries out a desorption step of recovering olefins by introducing the desorbents thereto through the conduit (6) and the valve (6c). The olefins discharged together with the desorbents from the adsorption tower (AD-3) is sent to the distillation tower (D2) through the valve (2c) and the conduit (2) and thus separated from the desorbent.

In addition, in the adsorption process, the adsorption tower (AD-1) after the pressure equalization step is depressurized through the valve (4a) and the conduit (4), and at that time, the discharged gas is introduced into the distillation tower (D1) (cocurrent depressurization step). During the cocurrent depressurization of the adsorption tower (AD-1), a C4 mixture gas is introduced into the adsorption tower (AD-2) through the conduit (1) and the valve (1b) and the adsorption tower (AD-2) carries out a step (pressurization step) of increasing the pressure to the adsorption pressure. At that time, the adsorption tower (AD-3) continues to carry out the desorption step.

The adsorption tower (AD-1) which just finished the cocurrent depressurization step carry out a C4 olefin rinse step, the adsorption tower (AD-2) carries out the adsorption step, and the adsorption tower (AD-3) continues to carry out the desorption step.

In this way, each adsorption tower carries out a sequential adsorption step—pressure equalization step—cocurrent depressurization step—C4 olefin rinse step—desorption step—pressure equalization step—pressurization step.

The pressure equalization step, the cocurrent depressurization step or the pressurization step can be omitted from the constitution of the process depending on the processing pressure of the adsorption step.

In addition, as can be seen in FIG. 4, the C4 olefins/paraffins mixture gas can be firstly distilled to give isobutane/butene-1 rich stream and normal butane/butene-2 rich stream and then the resulting isobutane/butene-1 rich stream can be fed into the adsorption process to obtain high purity butene-1, in place of obtaining high purity butene-1 by first processing the C4 olefins/paraffins mixture gas via the adsorption process to separate C4 olefins and then separating butene-1 from the resulting C4 olefins via the distillation process. In this case, paraffins, i.e., isobutane and olefin, i.e., butene-1 are separated by the same process as that described in said adsorption process.

Example 1

As shown in FIG. 1, the C4 mixture gas (table 2) was introduced into the adsorption process to separate C4 olefins and paraffins and then the separated C4 olefins was introduced into the distillation process to produce butene-1. The adsorption process was carried out by the facility of FIG. 2 according to the process constitutions of FIG. 3. With the cycle sequence as shown in FIG. 3 by using the apparatus as shown in FIG. 2, an experiment for separating olefins from a mixture gas of C4 olefins/paraffins was performed while using type 13X zeolite as an adsorbent for the separation of olefins/paraffins and using C5 mixture gas as a desorbent. The compositions of the C4 mixture gas and of the C5 mixture gas were shown in table 2. The C4 mixture gas was introduced into the adsorption process at the conditions of 60° C., 2000 mmHg and the flow rate of 1675 ml/min. A portion of high purity olefin containing gas obtained from the top of the distillation (D2) as shown in FIG. 2 was used in the C4 olefin rinse step, and the rinse flow rate was 300 ml/min. The high purity olefin containing gas obtained from the adsorption process was introduced into the distillation tower having 115-stage tray and thus obtained 99.54 wt % of butene-1 with a yield of 99.54 wt % at reflux ratio of 9. The composition of the products obtained from each of the conduits according to the method of FIG. 1 is presented in table 3.

TABLE 2

| Composition of C4 mixture gas and desorbents | |
|---|---|
| | Composition (wt %) |
| Components of mixture gas | |
| Iso-butane | 4.73 |
| Normal-butane | 15.3 |
| 1-Butene | 50.0 |
| Trans-2-butene | 19.0 |
| Cis-2-butene | 10.4 |
| Trace components | 0.57 |
| Components of desorbents | |
| Normal-pentane | 80.65 |
| Iso-pentane | 18.69 |
| Cyclopentane | 0.56 |
| Trace components | 0.10 |

TABLE 3

| Process performance obtained from Example 1 | | | | | | | | | | |
|---|---|---|---|---|---|---|---|---|---|---|
| Components | ml/min | wt % | ml/min | wt % | ml/min | wt % | ml/min | wt % | ml/min | wt % |
| Isobutane | | 4.73 | | 21.02 | | 0.16 | | 0.26 | | trace |
| Normal butane | | 15.3 | | 69.97 | | 2.23 | | 0.06 | | 5.86 |
| butene-1 | | 50.0 | | 6.73 | | 60.52 | | 99.52 | | 0.72 |
| Trans-2-butene | | 19.0 | | 2.27 | | 22.15 | | 0.15 | | 58.94 |
| Cis-2-butene | | 10.4 | | 0.9 | | 12.90 | | 1 ppm | | 34.47 |
| Total | 1675 | | 375 | | 1300 | | 27.20 | | 16.18 | |

In order to compare the process of the present invention with the process of the existing process, the yield and the purity of the butene-1 obtained by the hybrid process composed of the adsorption process and the distillation process according to the present invention and those of butene-1 obtained only by distillation as described in U.S. Pat. No. 4,718,986 are presented in table 4. The existing distillation process comprised a series of two distillation towers and these towers had the number of stages of 120 and 115 respectively, reflux ratio of 103 and 9 (on mass basis). The number of stage of the distillation tower used in the hybrid process of the adsorption process and the distillation process was 115 and the reflux ratio was 9. The yield increased by the hybrid process according to the present invention, and also installation costs and operation costs are reduced due to the reduction of one distillation tower with a large number of stage and a high reflux ratio.

TABLE 4

Yield and purity by the existing process and the invented process

| | Yield (wt %) | Purity (wt %) |
|---|---|---|
| Existing process(two distillation tower) | 91.35 | 99.50 |
| Adsorption tower + distillation tower | 93.00 | 99.58 |

INDUSTRIAL APPLICABILITY

The present invention is useful in reducing the butene-1 loss on eliminating isobutane and increasing the yield of butene-1 in the separation of butene-1 by using the hybrid process consisting of the adsorption process and the distillation process, as proved in the Examples of the present invention, since a portion of normal butane is removed together at the time of removing isobutane and thus the concentration of the normal butane introduced into the distillation tower for production of butene-1 is lowered.

Although the present invention has been described with respect to the exemplary embodiments in detail, these embodiments are intended only to be illustrative of the present invention and it is apparent to those skilled in the art that a variety of modifications and changes may be made without departing from the spirit and scope of the present invention.

The invention claimed is:

1. A method for separating butene-1 from a mixture gas of C4 olefins/paraffins by distilling C4 olefins obtained after the separation of the C4 olefins from a mixture gas of C4 olefins/paraffins by performing displacement desorption using desorbents, in a separating apparatus of several adsorption towers loaded with adsorbents which selectively adsorb olefins, a distillation tower for the separation of olefins/desorbents and a distillation tower for the separation of paraffins/desorbents, the method comprising:
   adsorbing olefins by introducing the mixture gas of C4 olefins/paraffins into the adsorption towers loaded with adsorbents and discharging non-adsorbed paraffins and the desorbents retained in the adsorption tower at the desorption step to the outlet of the adsorption tower and then discharging them to the distillation towers that separates parrafins and desorbents;
   rinsing with C4 olefin to increase the purity of olefins by introducing a portion of high purity C4 olefins resulting from the distillation process of olefins/desorbents into the adsorption towers after the completion of the adsorption and cleaning a small amount of paraffins adsorbed together with olefins;
   desorbing C4 olefins by introducing desorbents into the adsorption towers after the completion of the rinsing and discharging the mixture of olefins/desorbents to the distillation towers that separate olefins and desorbents to produce high purity olefins; and
   distilling the produced C4 olefins to obtain the butene-1.

2. The method for separating butene-1 from a mixture gas of C4 olefins/paraffins according to claim 1, wherein the adsorbing, rinsing, and desorbing are repeatedly performed at the adsorption towers.

3. The method for separating butene-1 from a mixture gas of C4 olefins/paraffins according to claim 1, further comprising: cocurrently depressurizing the adsorption towers to discharge the paraffins retained in the adsorption towers before the rinsing.

4. The method for separating butene-1 from a mixture as of C4 olefins/paraffins according to claim 1, further comprising:
   pressure equalization step at which the paraffin components present in the interior of the adsorption tower after the completion of the adsorbing step is transferred to the another adsorption tower which just completed the desorption step by connecting the two adsorption towers so that the pressure of the adsorption towers becomes equalized, and further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

5. The method for separating butene-1 from a mixture gas of C4 olefins/paraffins according to claim 1, where the desorbent separated from the olefin/desorbent distillation tower and the paraffin/desorbent distillation tower is recycled into the adsorption tower.

6. The method for separating butene-1 from a mixture gas of C4 olefins/paraffins according to claim 1, wherein the olefin selective absorbent is selected among the π-complex adsorbent forming π-complex selectively with olefins, type X zeolite or type Y zeolite.

7. The method for separating butene-1 from a mixture gas of C4 olefins/paraffins according to claim 1, wherein the operating pressure of the adsorption tower is 1 to 10 atm (absolute pressure) and the temperature is 20 to 150° C.

8. The method for separating butene-1 from a mixture gas of C4 olefins/paraffins according to claim 1, wherein the desorbent is C5 hydrocarbon or C6 hydrocarbon.

9. A method for separating butene-1 from a mixture gas of C4 olefins/paraffins by first distilling the mixture gas of the C4 olefins/paraffins to separate it into a mixture gas of normal butane and butene-2 and a mixture gas of isobutane and butene-1 and then performing displacement desorption using desorbents to separate butane-1 from the mixture gas of isobutene and butane-1, in an apparatus including a distillation tower for the separation of butene-1/desorbents, a distillation tower for the separation of isobutane/desorbents, and several adsorption towers loaded with adsorbents, which selectively adsorb butene-1, the method comprising:
   distilling the mixture gas of C4 olefins/paraffins to separate it into a mixture gas of normal butane and butene-2 and a mixture gas of isobutane and butene-1;
   adsorbing butene-1 by introducing the mixture gas of butene-1/isobutane into the adsorption towers loaded with adsorbents and discharging non-adsorbed isobutane and the desorbents retained in the adsorption tower at the desorption step to the outlet of the adsorption tower and then discharging them to the distillation towers that separates isobutane and desorbents;
   rinsing with butene-1 to increase the purity of butene-1 by introducing a portion of high purity butene-1 resulting from the distillation tower of butene-1/desorbents into the adsorption towers after the completion of the adsorption and cleaning a small amount of isobutene components adsorbed together with isobutane; and
   desorbing butene-1 by introducing desorbents into the adsorption towers after the completion of the rinsing and discharging the mixture of butene-1/desorbents to the distillation towers that separate butene-1 and desorbents to produce high purity butene-1.

10. The method for separating butene-1 from a mixture gas of C4 olefins/paraffins according to claim 9, wherein the adsorbing, rinsing, and desorbing are repeatedly performed at the adsorption towers.

11. The method for separating butene-1 from a mixture gas of C4 olefins/paraffins according to claim 9, further comprising: further comprising: cocurrently depressurizing the adsorption towers to discharge the paraffins retained in the adsorption towers before the rinsing.

12. The method for separating butene-1 from a mixture gas of C4 olefins/paraffins according to claim 9, further comprising:
pressure equalization step at which the paraffin components present in the interior of the adsorption tower after the completion of the adsorbing step is transferred to the another adsorption tower which just completed the desorption step by connecting the two adsorption towers so that the pressure of the adsorption towers becomes equalized, and further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

13. The method for separating butene-1 from a mixture gas of C4 olefins/paraffins according to claim 9, where the desorbent separated from the olefin/desorbent distillation tower and the paraffin/desorbent distillation tower is recycled into the adsorption tower.

14. The method for separating butene-1 from a mixture gas of C4 olefins/paraffins according to claim 9, wherein the olefin selective absorbent is selected among the π-complex adsorbent forming π-complex selectively with olefins, type X zeolite or type Y zeolite.

15. The method for separating butene-1 from a mixture gas of C4 olefins/paraffins according to claim 9, wherein the operating pressure of the adsorption tower is 1 to 10 atm (absolute pressure) and the temperature is 20 to 150° C.

16. The method for separating butene-1 from a mixture gas of C4 olefins/paraffins according, to claim 9, wherein the desorbent is C5 hydrocarbon or C6 hydrocarbon.

17. The method for separating butene-1 from a mixture gas of C4 olefins/paraffins according to claim 2, further comprising: cocurrently depressurizing the adsorption towers to discharge the paraffins retained in the adsorption towers before the rinsing.

18. The method for separating butene-1 from a mixture gas of C4 olefins/paraffins according to claim 2, further comprising:
pressure equalization step at which the paraffin components present in the interior of the adsorption tower after the completion of the adsorbing step is transferred to the another adsorption tower which just completed the desorption step by connecting the two adsorption towers so that the pressure of the adsorption towers becomes equalized, and further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

19. The method for separating butene-1 from a mixture gas of C4 olefins/paraffins according to claim 2, whew the desorbent separated from the olefin/desorbent distillation tower and the paraffin/desorbent distillation tower is recycled into the adsorption tower.

20. The method for separating butene-1 from a mixture gas of C4 olefins/paraffins according to claim 2, wherein the olefin selective absorbent is selected among the π-complex adsorbent forming π-complex selectively with olefins, type X zeolite or type Y zeolite.

21. The method for separating butene-1 front a mixture gas of C4 olefins/paraffins according to claim 2, wherein the operating pressure of the adsorption tower is 1 to 10 atm (absolute pressure) and the temperature is 20 to 150° C.

22. The method for separating butene-1 from a mixture gas of C4 olefins/paraffins according to claim 2, wherein the desorbent is C5 hydrocarbon or C6 hydrocarbon.

23. The method for separating butene-1 from a mixture gas of C4 olefins/paraffins according to claim 10, further comprising: further comprising: cocurrently depressurizing the adsorption towers to discharge the paraffins retained in the adsorption towers before the rinsing.

24. The method for separating butene-1 from a mixture gas of C4 olefins/paraffins according to claim 10, further comprising:
pressure equalization step at which the paraffin components present in the interior of the adsorption tower after the completion of the adsorbing step is transferred to the another adsorption tower which just completed the desorption step by connecting the two adsorption towers so that the pressure of the adsorption towers becomes equalized, and further includes a cocurrent depressurization step of discharging the paraffin components present in the adsorption towers after the pressure reduction through the pressure equalization step, and a pressurization step which pressurize the adsorption tower to the adsorption pressure by introducing the mixture gas of C4 olefins/paraffins into the adsorption tower partially pressurized through the pressure equalization step.

25. The method for separating butene-1 from a mixture gas of C4 olefins/paraffins according to claim 10, where the desorbent separated from the olefin/desorbent distillation tower and the paraffin/desorbent distillation tower is recycled into the adsorption tower.

26. The method for separating butene-1 from a mixture gas of C4 olefins/paraffins according to claim 10, wherein the olefin selective absorbent is selected among the π-complex adsorbent forming π-complex selectively with olefins, type X zeolite or type Y zeolite.

27. The method for separating butene-1 from a mixture gas of C4 olefins/paraffins according to claim 10, wherein the operating pressure of the adsorption tower is 1 to 10 atm (absolute pressure) and the temperature is 20 to 150° C.

28. The method for separating butene-1 from a mixture gas of C4 olefins/paraffins according to claim 10, wherein the desorbent is C5 hydrocarbon or C6 hydrocarbon.

* * * * *